US00PP33890P2

(12) United States Plant Patent
Li

(10) Patent No.: US PP33,890 P2
(45) Date of Patent: Jan. 18, 2022

(54) ***LAVANDULA* PLANT NAMED 'KLELV20123'**

(50) Latin Name: *Lavandula angustifolia*
Varietal Denomination: KLELV20123

(71) Applicant: Klemm+Sohn GmbH & Co. KG, Stuttgart (DE)

(72) Inventor: Ruijun Li, North Parramatta (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/331,285

(22) Filed: May 26, 2021

(51) Int. Cl.
*A01H 5/02* (2018.01)
*A01H 6/50* (2018.01)

(52) U.S. Cl.
USPC ..... Plt./445
CPC ..... *A01H 6/502* (2018.05)

(58) Field of Classification Search
USPC ..... Plt./445
CPC ..... A01H 6/502; A01H 5/02
See application file for complete search history.

*Primary Examiner* — Keith O. Robinson
(74) *Attorney, Agent, or Firm* — Weatherly IP Solutions, LLC; Barbara Campbell

(57) ABSTRACT

A new *Lavandula* plant particularly distinguished by early flowering, good branching, and dark-purple bracts, is disclosed.

1 Drawing Sheet

Genus and species: *Lavandula angustifolia.*
Variety denomination: 'KLELV20123'.

BACKGROUND OF THE NEW PLANT

The present invention comprises a new and distinct variety of *Lavandula*, botanically known as *Lavandula angustifolia*, and hereinafter referred to by the variety name 'KLELV20123'. 'KLELV20123' originated from a cross-pollination conducted in November 2011 in Cobbitty, New South Wales, Australia between the proprietary female parent 'LS1009' (unpatented) and the proprietary male parent 'LS1012' (unpatented).

The seeds from the cross were sown and plants were grown outdoors for evaluation, where an individual plant designated 'KLELV20123' was selected from the group of plants in September 2012 in Cobbitty, New South Wales, Australia. 'KLELV20123' was first vegetatively propagated by stem cuttings in October 2012 in Cobbitty, New South Wales, Australia. 'KLELV20123' was found to reproduce true to type in successive generations of asexual propagation via vegetative stem cuttings.

SUMMARY

The following are the most outstanding and distinguishing characteristics of this new variety when grown under normal horticultural practices in Stuttgart, Germany.

1. Early flowering;
2. Good branching; and
3. Dark-purple bracts.

DESCRIPTION OF THE PHOTOGRAPH

This new *Lavandula* plant is illustrated by the accompanying photograph which shows the plant's overall plant habit including form, foliage, and flowers. The photograph is of a 14-week-old plant grown in a greenhouse in Stuttgart, Germany in August 2020. The colors shown are as true as can be reasonably obtained by conventional photographic procedures.

DESCRIPTION OF THE NEW VARIETY

The following detailed descriptions set forth the distinctive characteristics of 'KLELV20123'. The data which define these characteristics were collected from asexual reproductions carried out in Cobbitty, New South Wales, Australia in November 2019. Data was collected on four-month-old plants grown outdoors. Color references are to The R.H.S. Colour Chart of The Royal Horticultural Society of London (R.H.S.), 5$^{th}$ edition (2007).

Classification:
- *Family.*—Asteraceae.
- *Botanical.*—*Lavandula angustifolia.*
- *Common.*—*Lavandula,* lavender.
- *Designation.*—'KLELV20123'.

Parentage:
- *Female parent.*—The proprietary female *Lavandula* variety 'LS1009' (unpatented).
- *Male parent.*—The proprietary male *Lavandula* variety 'LS1012' (unpatented).

Plant:
- *Propagation type.*—Vegetative stem cuttings.
- *Time to initiate roots.*—10 to 12 days.
- *Time to produce a rooted cutting.*—Approximately 3 to 4 weeks.
- *Root description.*—Fine, fibrous; white in color, RHS 155C (White).
- *Rooting habit.*—Freely branching.
- *Plant habit.*—Compact and upright.
- *Growth rate.*—Rapid.
- *Vigor.*—Moderate.
- *Plant height.*—29.0 cm.
- *Plant diameter or spread.*—21.0 cm.
- *Attitude of the outer flowering stems at full flowering of the plant.*—Erect.
- *Density of the plant at full flowering.*—Medium.

Lateral branches:
*Quantity of lateral branches:* 26-31.
*Length.*—15.0 cm.
*Diameter.*—0.24 cm.
*Stem internode length.*—1.2 cm.
*Number of internodes per branch/stem.*—9 to 13.
*Texture.*—Pubescent.
*Color.*—Young stems are RHS 138B (Green); mature stems are RHS 138C (Green).
*Stem shape.*—Quadrangular.
*Strength.*—Strong.

Leaves:
*Arrangement.*—Opposite.
*Leaf type.*—Simple.
*Quantity per main branch.*—10 to 13 pairs fully expanded.
*Length.*—3.2 cm.
*Width.*—0.64 cm.
*Shape.*—Lanceolate.
*Apex.*—Acute.
*Base.*—Truncate.
*Margin.*—Entire.
*Attachment.*—Sessile.
*Fragrance.*—Very strong lavender scent.
*Texture* (*both upper and lower surface*).—Pubescent.
*Immature leaf color.*—Upper surface: RHS 191B (Greyed-Green). Lower surface: RHS 191B (Greyed-Green).
*Mature leaf color.*—Upper surface: RHS 191A (Greyed-Green). Lower surface: RHS 191C (Greyed-Green).
*Venation pattern.*—Pinnate.
*Venation color* (*both upper and lower surfaces*).—RHS 191B (Greyed-Green).
*Petiole.*—Absent.

Flower buds:
*Length.*—0.5 cm.
*Diameter.*—About 0.16 cm.
*Shape.*—Oblong.
*Color.*—RHS 96C (Violet-Blue).
*Rate of opening.*—High.

Flowers:
*Form.*—Small, single flower in verticillasters arranged in spikes.
*Number of rows of flowers.*—9.
*Number of flower spikes per lateral stem.*—1.
*Average number of flowers per spike.*—90 to 117.
*Inflorescence length* (*excluding terminal bracts*).—6.2 cm.
*Inflorescence width* (*excluding terminal bracts*).—2.4 cm.
*Flower longevity.*—2 to 3 weeks.
*Self-cleaning or persistent.*—Self-cleaning.
*Fragrance.*—None detected.
*Natural flowering season.*—From winter to late spring in Australia.
*Position of flowers relative to the foliage.*—Moderately above.

Petals:
*Shape.*—Salverform.
*Quantity of petals.*—5, fused.
*Length.*—0.5 cm.
*Width.*—0.2 cm.
*Shape.*—Ovate.
*Apex.*—Rounded.
*Base.*—Fused.
*Margin.*—Entire.
*Texture* (*both upper and lower surfaces*).—Glabrous.
*Color, immature* (*both upper and lower surfaces*).—RHS N79A (Purple).
*Color, mature* (*both upper and lower surfaces*).—RHS N79A (Purple).

Calyx:
*Quantity of sepals and arrangement.*—5, and all of the sepals are fused into a campanulate tube.
*Calyx shape.*—Flattened tube.
*Calyx length.*—0.3 cm.
*Calyx width.*—0.15 cm.
*Sepal texture* (*both upper and lower surfaces*).—Tomentose.
*Sepal color* (*both upper and lower surfaces*).—RHS 145B (Yellow-Green) and close to RHS 145C (Yellow-Green) at the base.
*Sepal shape.*—Lanceolate.
*Sepal apex.*—Acute.
*Sepal margin.*—Entire.

Terminal bracts:
*Quantity.*—4 to 7.
*Attitude and angle of attachment.*—Each whorl of flowers subtended by dry bracts and 8 to 10 whorls per spike; 4 to 7 bracts arising at a 10 to 15 degree angle from the top of the inflorescence.
*Infertile bracts of the spikes.*—Present.
*Length.*—2.5 cm.
*Width.*—1.4 cm.
*Texture* (*both upper and lower surfaces*).—Smooth.
*Shape.*—Oblanceolate.
*Apex.*—Acute.
*Base.*—Oblique.
*Margin.*—Entire.
*Venation pattern.*—Reticulate.
*Venation color.*—RHS 83A (Violet).
*Duration on plant.*—8 to 12 weeks with good color.
*Self-cleaning or persistent.*—Persistent.
*Color* (*both upper and lower surfaces*).—RHS N82B (Purple-Violet).

Peduncles:
*Length.*—3.6 cm to 4.1 cm.
*Diameter.*—0.25 cm.
*Strength.*—Moderate.
*Texture.*—Pubescent.
*Color.*—RHS 138B (Green).
*Aspect.*—Straight.

Reproductive organs:
*Stamens.*—Quantity per flower: 4. Filament length: 0.25 cm. Filament color: RHS 75C (Purple). Anther length: 0.05 cm. Anther diameter: 0.03 cm. Anther color: RHS N155A (White). Pollen amount: Sparse. Pollen color: RHS 2D (Yellow-Green).
*Pistils.*—Quantity per flower: 1. Pistil length: 0.3 cm. Style length: 0.25 cm. Style color: RHS 75C (Purple). Stigma shape: Club-shaped. Stigma length: 0.05 cm. Stigma color: RHS N98B (Violet-Blue). Ovary size: Too small to measure.

Fruit and seed set: None observed.

Disease and pest/insect resistance: No disease and pest/insect resistance observed.

COMPARISON WITH PARENTAL LINES AND KNOWN VARIETY

'KLELV20123' is distinguished from its parents as described in Table 1.

TABLE 1

| Comparison with Parental Lines | | | |
|---|---|---|---|
| Characteristic | 'KLELV20123' | Female Parent 'LS1009' | Male Parent 'LS1012' |
| Earliness to flower | Early | Later than 'KLELV20123' | Later than 'KLELV20123' |
| Branching | More branching than the parental lines | Less branching than 'KLELV20123' | Less branching than 'KLELV20123' |
| Bract color | Dark-purple | Pink-purple | Dark-purple |

'KLELV20123' is most similar to the commercial *Lavandula* variety 'Madrid Purple' (unpatented). Differences between the varieties are described in Table 2.

TABLE 2

| Comparison with Similar Variety | | |
|---|---|---|
| Characteristic | 'KLELV20123' | 'Madrid Purple' |
| Earliness to flower | 1 to 2 weeks earlier than 'Madrid Purple' | Later than 'KLELV20123' |
| Branching | More branching than 'Madrid Purple' | Less branching than 'KLELV20123' |

I claim:

1. A new and distinct variety of *Lavandula* plant designated 'KLELV20123' as illustrated and described herein.

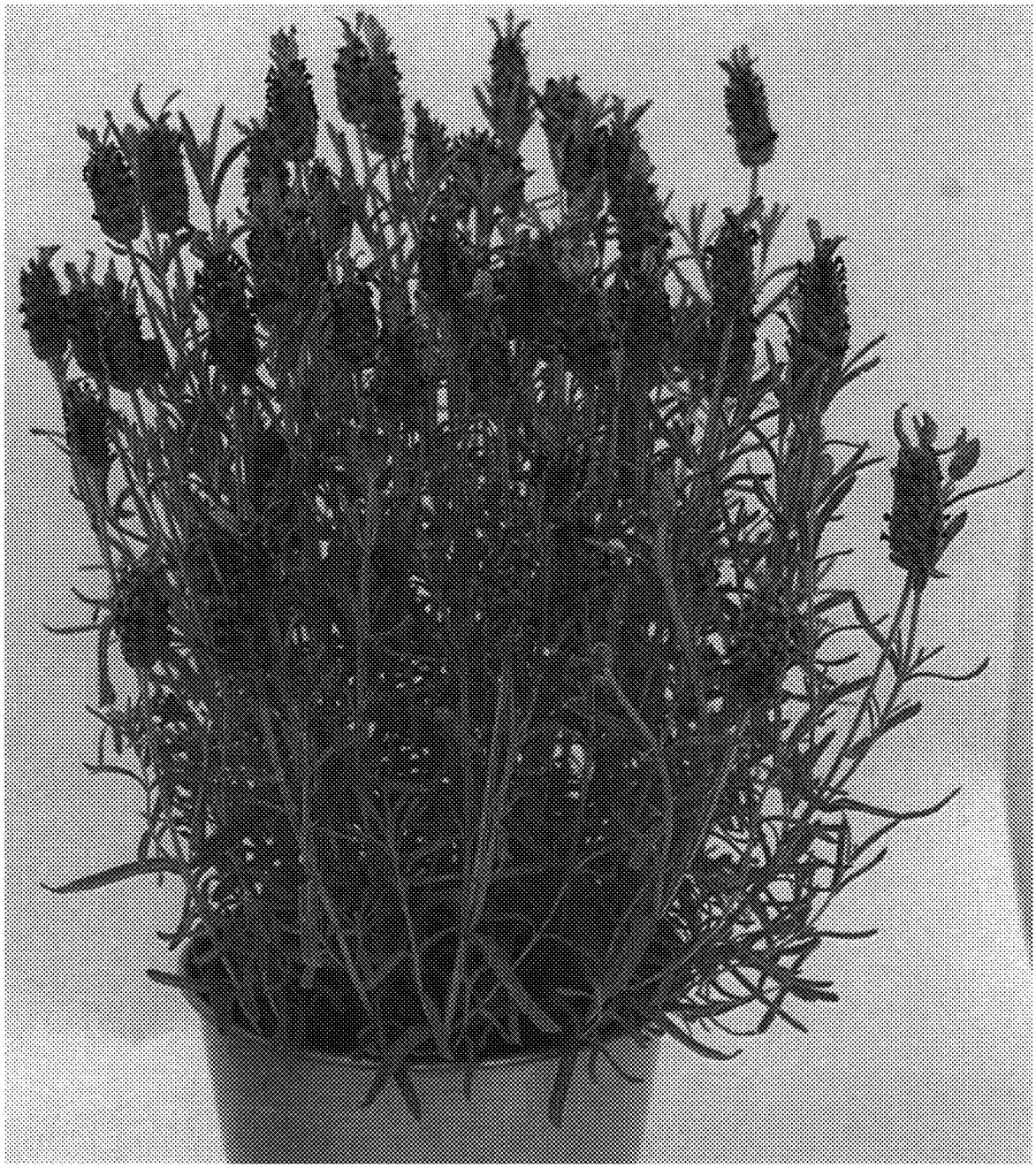

* * * * *